US008770753B2

(12) United States Patent
Hee et al.

(10) Patent No.: US 8,770,753 B2
(45) Date of Patent: Jul. 8, 2014

(54) SCANNING AND PROCESSING USING OPTICAL COHERENCE TOMOGRAPHY

(75) Inventors: Michael Hee, Burlingame, CA (US); Jay Wei, Fremont, CA (US); David Huang, Portland, OR (US); Qienyuan Zhou, Del Mar, CA (US); Yonghua Zhao, Pleasanton, CA (US); Ben Jang, Cupertino, CA (US); Tony Ko, Cupertino, CA (US)

(73) Assignee: Optovue, Inc., Fremont, CA (US)

( * ) Notice: Subject to any disclaimer, the term of this patent is extended or adjusted under 35 U.S.C. 154(b) by 27 days.

(21) Appl. No.: 13/310,626

(22) Filed: Dec. 2, 2011

(65) Prior Publication Data

US 2012/0140174 A1 Jun. 7, 2012

Related U.S. Application Data

(60) Provisional application No. 61/419,800, filed on Dec. 3, 2010.

(51) Int. Cl.
*A61B 3/14* (2006.01)
*A61B 3/10* (2006.01)
*A61B 3/12* (2006.01)

(52) U.S. Cl.
CPC . *A61B 3/102* (2013.01); *A61B 3/14* (2013.01); *A61B 3/1225* (2013.01)
USPC .......................................................... 351/206

(58) Field of Classification Search
USPC ................................ 351/205, 206, 246; 606/4
See application file for complete search history.

(56) References Cited

U.S. PATENT DOCUMENTS

| 7,744,221 | B2 | 6/2010 | Wei et al. |
| 2007/0195269 | A1 | 8/2007 | Wei et al. |
| 2008/0181477 | A1 | 7/2008 | Izatt et al. |
| 2008/0309881 | A1 | 12/2008 | Huang et al. |
| 2009/0161827 | A1 | 6/2009 | Gertner et al. |

FOREIGN PATENT DOCUMENTS

WO      WO 2010/129544 A1      11/2010

OTHER PUBLICATIONS

PCT International Search Report mailed Mar. 29, 2012, in related International Application No. PCT/US2011/063185.
Coolens et al., "Implementation and Characterization of a 320-slice Volumetric CT Scanner for Simulation in Radiation Oncology", *Med. Phys.*, vol. 36, Issue 11, 2009.
Huang et al., "Intraretinal Segmentation on Fourier Domain Optical Coherence Tomography", *Annals Academy of Medicine*, vol. 39, No. 7, Jul. 2010.

(Continued)

*Primary Examiner* — Mahidere Sahle
(74) *Attorney, Agent, or Firm* — Haynes and Boone, LLP

(57) ABSTRACT

In accordance with some embodiments, a method of eye examination includes acquiring OCT data with a scan pattern centered on an eye cornea that includes n radial scans repeated r times, c circular scans repeated r times, and n* raster scans where the scan pattern is repeated m times, where each scan includes a A-scans, and where n is an integer that is 0 or greater, r is an integer that is 1 or greater, c is an integer that is 0 or greater, n* is an integer that is 0 or greater, m is an integer that is 1 or greater, and a is an integer greater than 1, the values of n, r, c, n*, and m being chosen to provide OCT data for a target measurement, and processing the OCT data to obtain the target measurement.

10 Claims, 20 Drawing Sheets

710

(56) References Cited

OTHER PUBLICATIONS

Sull et al., "Comparison of Spectral/Fourier Domain Optical Coherence Tomography Instruments for Assessment of Normal Macular Thickness", *National Institutes of Health*—PA Author Manuscript, Feb. 2010.

O. Tan et al., "Detection of Macular Ganglion Cell Loss in Glaucoma by Fourier-Domain Optical Coherence Tomography", Ophthalmology, 116(12):2305-2314, 2009.

International Preliminary Report on Patentability mailed Jun. 13, 2013, in related International Application No. PCT/US2011/063185.

a b

SCANNING AND PROCESSING USING OPTICAL COHERENCE TOMOGRAPHY

RELATED APPLICATIONS

This application claims priority to U.S. Provisional Application 61/419,800, filed on Dec. 3, 2010, which is herein incorporated by reference in its entirety.

BACKGROUND

1. Field of the Invention

The embodiments described herein relate generally to methods and systems for collecting and processing images in ophthalmology for diagnostics and treatment of a disease or any other physiological condition.

2. Description of Related Art

Optical Coherence Tomography (OCT) is an optical signal imaging and processing technique that captures three-dimensional (3D) data sets with micrometer resolution. This OCT imaging modality has been commonly used for non-invasive imaging of an object of interest, such as the retina of the human eye for example, over the past 15 years. A cross sectional retinal image as a result of an OCT scan allows users and clinicians to evaluate various kinds of ocular pathologies in the field of ophthalmology. However, due to limitations of scan speed in imaging devices based on time-domain technology (TD-OCT), only very limited number of cross-sectional image can be obtained for evaluation and examination of the entire retina.

A new generation of OCT technology, Fourier-Domain or Spectral Domain Optical Coherence Tomography (FD/SD-OCT), is significantly improved from TD-OCT, reducing many of the limitations of OCT such as data scan speed and resolution. 3D data set with dense raster scan or repeated cross-sectional scans can now be achieved by FD-OCT with a typical scan rate of approximately 17,000 to 40,000 A-scans per second. Newer generations of FD-OCT technology will likely further increase scan speeds to 70,000 to 100,000 A-scans per second.

Therefore, there is a need for better, more systematic, systems to collect and analyze OCT data.

SUMMARY

In accordance with some embodiments, a method of eye examination includes acquiring OCT data with a scan pattern centered on an eye cornea that includes n radial scans repeated r times, c circular scans repeated r times, and n* raster scans where the scan pattern is repeated m times, where each scan includes a A-scans, and where n is an integer that is 0 or greater, r is an integer that is 1 or greater, c is an integer that is 0 or greater, n* is an integer that is 0 or greater, m is an integer that is 1 or greater, and a is an integer greater than 1, the values of n, r, c, n*, and m being chosen to provide OCT data for a target measurement, and processing the OCT data to obtain the target measurement.

In some embodiments, an OCT imaging system includes an OCT imager that acquires OCT data with a scan pattern centered on an eye cornea that includes n radial scans repeated r times, c circular scans repeated r times, and n* raster scans where the scan pattern is repeated m times, where each scan includes a A-scans, and where n is an integer that is 0 or greater, r is an integer that is 1 or greater, c is an integer that is 0 or greater, n* is an integer that is one or greater, m is an integer that is 1 or greater, and a is an integer greater than 1, the values of n, r, c, n*, and m being chosen to provide OCT data for a target measurement, and a computer that processes the OCT data to obtain the target measurement.

BRIEF DESCRIPTION OF THE DRAWINGS

FIG. 3b is an example of a pachymetry map obtained by the steps illustrated in FIG. 3a.

DETAILED DESCRIPTION

Optical Coherence Tomography (OCT) technology has been commonly used in the medical industry to obtain information-rich content in three-dimensional (3D) data sets. OCT can be used to provide imaging for catheter probes during surgery. In the dental industry, OCT has been used to guide dental procedures. In the field of ophthalmology, OCT is capable of generating precise and high resolution 3D data sets that can be used to detect and monitor different eye diseases in the cornea and the retina. Different scan configurations have been developed for different industries and for different clinical applications. For example, a scan configuration had been designed to obtain information in the ganglion cell complex (GCC) (see US Pat. App. Pub. 2008/0309881). GCC has been demonstrated to provide accurate information useful for clinical diagnosis for the disease of glaucoma (see Tan O. et al., [Ophthalmology, 116:2305-2314 (2009)]). Other useful scan configurations and methods have also been disclosed (see, for example, U.S. Pat. No. 7,744,221).

Specific scan configurations can be utilized for specific clinical applications. Some embodiments of different scan configurations are also disclosed in the following. These scan configurations further expand the application of OCT technology for different clinical applications and further enhance the quality and information-richness of 3D data set obtained by OCT technologies.

Technological advances in data collection systems are capable of generating massive amounts of data at ever increasing rates. As a result of these developments, myriad scan patterns can be employed to capture different areas of interest with different directions and orientations. A system of scan pattern design that more systematically captures 3D data sets and sets a standard and consistent expectation of scan patterns for different clinical needs is disclosed. In some embodiments, the scan pattern substantially covers a cornea region. In some embodiments, the scan pattern includes a plurality of radial lines and at least one circle wherein the radial lines intersect at the center of the circle. Systems and methods to process these 3D data sets are also disclosed in the present invention. In some embodiments, the OCT images are processed and at least one characteristic of the cornea region is determined.

Figure 6A:
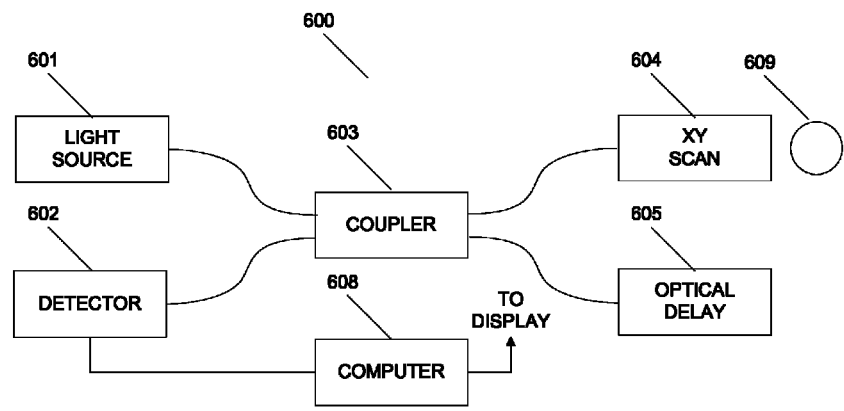
FIG. 6a illustrates an example of an OCT imager.

FIG. 6a illustrates an example of an OCT imager 600 that can be utilized in enhancing an OCT data set according to some embodiments of the present invention. OCT imager 600 includes light source 601 supplying light to coupler 603, which directs the light through the sampling arm to XY scan 604 and through the reference arm to optical delay 605. XY scan 604 scans the light across object 609, which may be an eye, and collects the reflected light from object 609. Light reflected from object 609 is captured in XY scan 604 and combined with light reflected from optical delay 605 in coupler 603 to generate an interference signal. The interference signal is coupled into detector 602. OCT imager 600 can be a time domain OCT imager, in which case depth (or A-scans) are obtained by scanning optical delay 605, or a Fourier domain imager, in which case detector 602 is a spectrometer that captures the interference signal as a function of wavelength. In either case, the OCT A-scans are captured by computer 608. Collections of A-scans taken along an XY pattern are utilized in computer 608 to generate 3-D OCT data sets. Computer 608 can also be utilized to process the 3-D OCT data sets into 2-D images according to some embodiments of the present invention. Computer 608 can be any device capable of processing data and may include any number of processors or microcontrollers with associated data storage such as memory or fixed storage media and supporting circuitry.

Figure 6B:
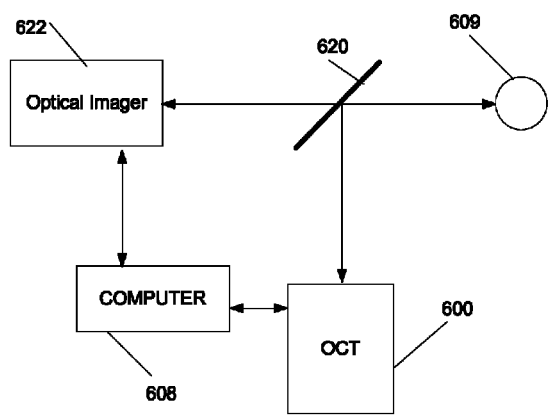
FIG. 6b illustrates the combination of an OCT imager with another optical imaging modality.

FIG. 6b illustrates a system where OCT imager 600 is combined with another optical imager 622. Optical imager 622 can be, for example, a corneal topography imager, video imagers, retina adaptor, or other optical devices. Light beams from optical imager 622 and OCT 600 can be combined and directed onto object 609 with, for example, a beam splitter 620. Both optical imager 622 and OCT 600 can be controlled, and images from each obtained and processed in computer 608. Computer 608 can be any standard computer and may include user interfaces such as, for example, keyboards, touchscreens, pointer devices, video screens, and audio devices. Computer 608 may include memory and fixed data storage devices in order to store and process images and store and execute programs for data analysis and imager control.

Part A. Design of Scan Patterns

Figure 1:
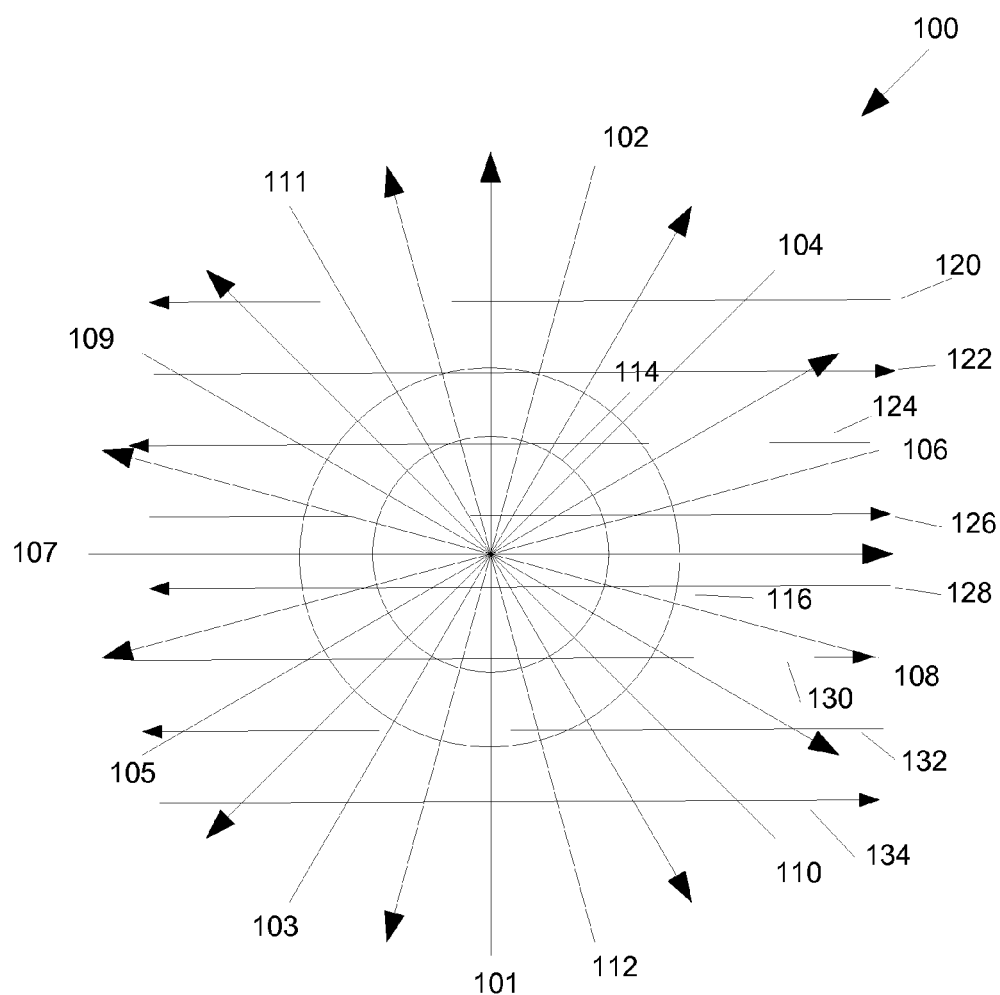
FIG. 1 shows an exemplary scan configuration suitable for corneal pachymetry and topography.

FIG. 1 illustrates an exemplary scan configuration 100 according to some embodiment of the present invention that can be utilized in the OCT imager 600 illustrated in FIG. 6. Scan configuration 100 follows a systematic scan pattern design scheme that is suitable to obtain OCT data sets for different measurements and applications for corneal and anterior segment measurements, such as corneal pachymetry and topography measurements.

As shown in FIG. 1, scan configuration 100 includes radial B-scans (radial scans 101 through 112 are illustrated), circular B-scans (scans 114-116 are illustrated), and horizontal raster B-scans (scans 120-134 are illustrated). In general, there can be any number of radial scans, any number of circular scans, and any number of horizontal scans in scan configuration 100. Along the scan configuration 100, A-scan data is obtained. Additionally, scan directions (e.g., vertical scans) can also be included. In general, a scan pattern adapted for particular types of analysis can be devised utilizing the generalized scan pattern illustrated in FIG. 1.

Scan pattern 100 can be characterized by the following parameters, namely:

a represents the number of A-scans per B-scan;

r represents the number of repeated radial (meridian) scans 101-112, where r=1, 2, 3, . . . , R;

n represents the number of radial (meridian) scans 101-112, where n=0, 1, 2, 3, . . . , N;

n* represents the number of raster (horizontal line) scans 120-134, where n*=0, 1, 2, 3, . . . , N;

c represents the number of circular scans 114-116, where c=0, 1, 2, 3, . . . , C;

m represents the number of repeated scan pattern 100, where m=1, 2, 3, . . . , M; and t represents the total scan time.

These parameters can be adjusted to produce optimal scanning features depending on applications and informational data that are desired. For instance, increasing the number of A-scans per B-scan would generally yield an image of better quality, but it will likely take a longer time t to scan because of the increase in the number of A-scans. Increasing the number of repeated meridian scans r within each scan pattern would likely increase the time to scan the desired data; however, the increase in r can allow important information to be captured in order to detect instantaneous eye movement in-between the repeated radial scans. In the same manner, the additional data obtained with repeated radial scans can further enhance the scan quality and reliability by performing scan average for the repeated data. Since scan pattern 100 includes both radial and circular scans, OCT data are denser near the center of the scan pattern and are less dense at the periphery. Increasing the number of radial scans n and/or circular scans c can increase the scan density at the periphery and thus preventing relevant features to be undetected as in the case of a coarser scan configuration. A circular scan such as scan 114 is preferably coaxial to the center of the radial scans (scans 101-112) and this scan type can be used for scan registration and/or data tilt detection, such as corneal tilt detection. The lengths of radial scans 101-112 and the diameter of the circular scan 114 can be designed to suit a particular need. In additional to optical coherence tomography (OCT), the above mentioned scan pattern design can be applied to other imaging modalities, such as ultrasound technology.

The total scan time t is one of the major concerns in the design of scan patterns. In the field of ophthalmology, the human eye produces microsaccadic motions several tens of times per second, and motion artifacts can usually be observed when the total scan time increases. The total scan time t for a complete scan pattern, governed by the parameters mentioned above [a, r, (n+c), m], can be calculated by $$t=(a \times r \times (n+c) \times m)/S,$$

where S is the scanning speed of the imaging system being used. For only the raster scans are taken, the total scan time becomes $$t=(a \times r \times n^* \times m)/S.$$

It is noted that the scan direction and scan order of scan segments (radial and circular scans) can be arranged to minimize travel distances between one end-point of one scan segment to a start-point of another scan segment. Multiple repetitions m of a scan pattern, each containing a set of radial and circular segments, can provide valuable information to enhance the scan quality and reliability of further data processing. In a set of n radial scans, information on the x-y position of the pupil of a subject eye 609 and the 3-dimensional orientation (tilt angle in the x-z and y-z planes) of the cornea of object eye 609 can be obtained. By comparing the pupil position and corneal tilt of succeeding OCT scan sets, movement of the eye can be detected and compensated in further data processing and measurements evaluation, such as measurements for corneal power calculation, pachymetry map and topography map generation.

As a short-cut notation to identify a particular scan pattern, each scan pattern can be designated [a, r, (n+c+n*), m]. A particular scan pattern that includes only radial and circular scans can be designated as [a, r, (n+c), m]. Radial scans in this designation are equally angularly separated unless otherwise specified. Circular scans are co-centric and centered on the intersection of the radial scans. Horizontal scans have equal separation between scans and the center of the block covered by the horizontal scans is co-centric with the intersection of the radial scans and the center of the circular scans. Additionally, the order in which the scan pattern is executed can be arranged to optimize the overall timing. For example, radial scans 101-112 of FIG. 1 illustrate with arrows the direction of each radial scan and are arranged such that the repositioning of the OCT beam is minimal between different scans, decreasing the time it takes OCT 600 to set up for each individual scan in scan pattern 100.

Several different scan patterns are provided below. These scan patterns are specific to particular data analysis and are provided as examples for obtaining high quality measurements of eye parameters. If object 609 is not an eye, then other scan patterns may be obtained according to aspects of the present invention. In each case, scan patterns 100 illustrated below provide sufficient density of OCT data to reliably and accurately measure the particular parameters that are sought.

A1. Pachymetry Scan Pattern [1024, 2, (12+1), 3]

Scan configuration 100 in FIG. 1 employs the design scheme as discussed above. A [1024, 2, (12+1), 3] scan pattern can be particularly useful for Pacymetry scans. In this scan configuration, there are twelve radial scans 101-112 (n=12) plus one circular scan 114 (c=1), repeated two times (r=2), in each scan set and such scan set is repeated three times (m=3) to create this scan pattern. In some embodiments, the lengths of the radial segments 101-112 can be about 11 mm and the diameter of the circular segment 114 can be about 3 mm. The scan configuration 100 is suitable for obtaining corneal pachymetry and topography map to cover an area of interest of about 11 mm in diameter. The length of each radial scan 101-112, generally ranges from about 9 to about 12 mm.

The diameter of the circular scan can vary, depending on the area of interest. The approximate total scan time for scan pattern 100 with a=1024 is t=(1024×2×(13)×3)/70,000=1.14 sec, assuming a scan speed of 70,000 A-scans/second. The total scan time t will vary depending on the scan speed of the OCT scanner.

In each of the radial segment 101-112 in scan configuration 100, each segment can be repeated multiple times, for example two times, in the direction of the arrow in each respective segment in 100. As shown in FIG. 1, the scan configuration begins with scan segment 101 in the direction of the arrow, and then scan segment 102 was scanned in the direction of the arrow 102, beginning at the end point of scan segment 101. This scan arrangement is used to minimize the travel distance between successive scan segments to reduce the total scan time t. This scan arrangement continues until scan segment 112 is completed, and then the circular scan segment 114 can then be acquired. This completes one set of scan configuration 100, and this same scan configuration set can then be repeated, for example three times. Different arrangements of scan order can be understood by one of ordinary skill in the art within the scope of the present invention. For example, the circular scan 114 can be the first scan segment, followed by radial scan 101. In another example, the radial scan can be repeated less or more than twice and can be in opposition direction to each other to minimize travel time, instead of following the direction as in FIG. 1.

A2. Corneal Power Scan Pattern [1024, 2, (8+1), 3]

Figure 2:
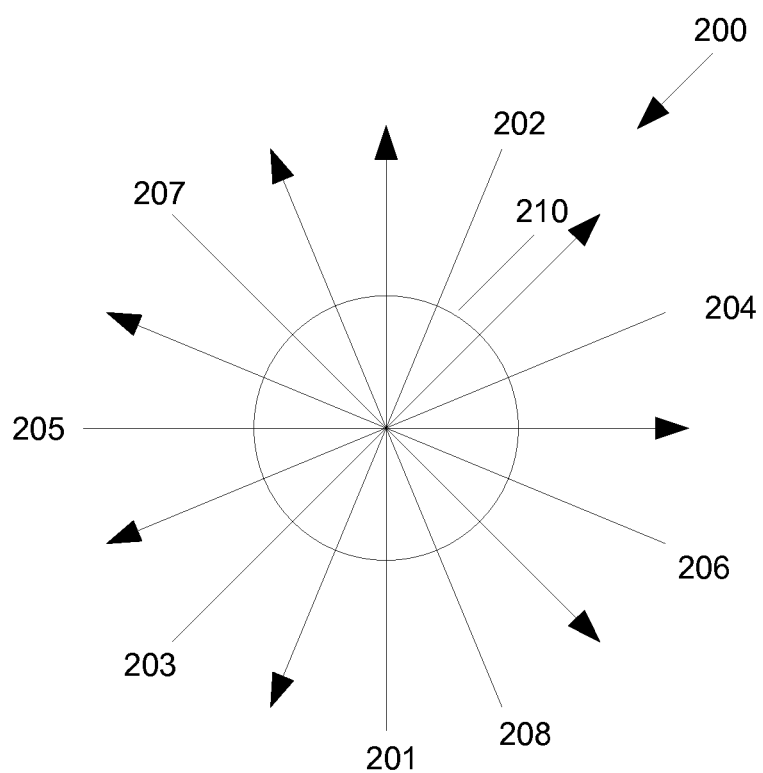
FIG. 2 shows an exemplary scan configuration suitable for measurement of cornea power.

Scan configuration 200 illustrated in FIG. 2 is another example scan pattern 100 configuration using the systematic design approach described above. Scan pattern 200 can be designated as [1024, 2, (8+1), 3]. In scan pattern 200, there are eight radial scans 201-208 plus one circular scan 210, repeated two times (r=2), in each scan set. The scan set is repeated three time (m=3) to create this scan pattern 200. In some embodiments, the lengths of the radial segments 201-208 are about 6 mm and the diameter of the circular segment 210 is about 3 mm. The scan configuration 200 is suitable for obtaining corneal power measurements for an area of interest of up to about 6 mm in diameter. The approximate total scan time for scan pattern 200, with a=1024, is t=(1024×2×(9)×3)/70,000=0.79 sec, assuming a scan speed of 70,000 A-scans/second. Other variations and arrangements can be readily applied in this scan design as described in FIG. 2.

Similarly, different number of radial scans and circular scans can be used in the scan pattern 200 if desired. For examples, sixteen radial scan can be used to further increase the scan density at the periphery of scan pattern 200 to reduce the chance of missing small corneal features, as in the case in coarser scans. A larger, radial scans with length of about 18 mm, scan pattern 200 can be used to cover the corneal and anterior scleral surfaces of the eye. This larger scan area of the eye can provide useful information, for example, in assisting contact lens fitting and design.

Figure 7:
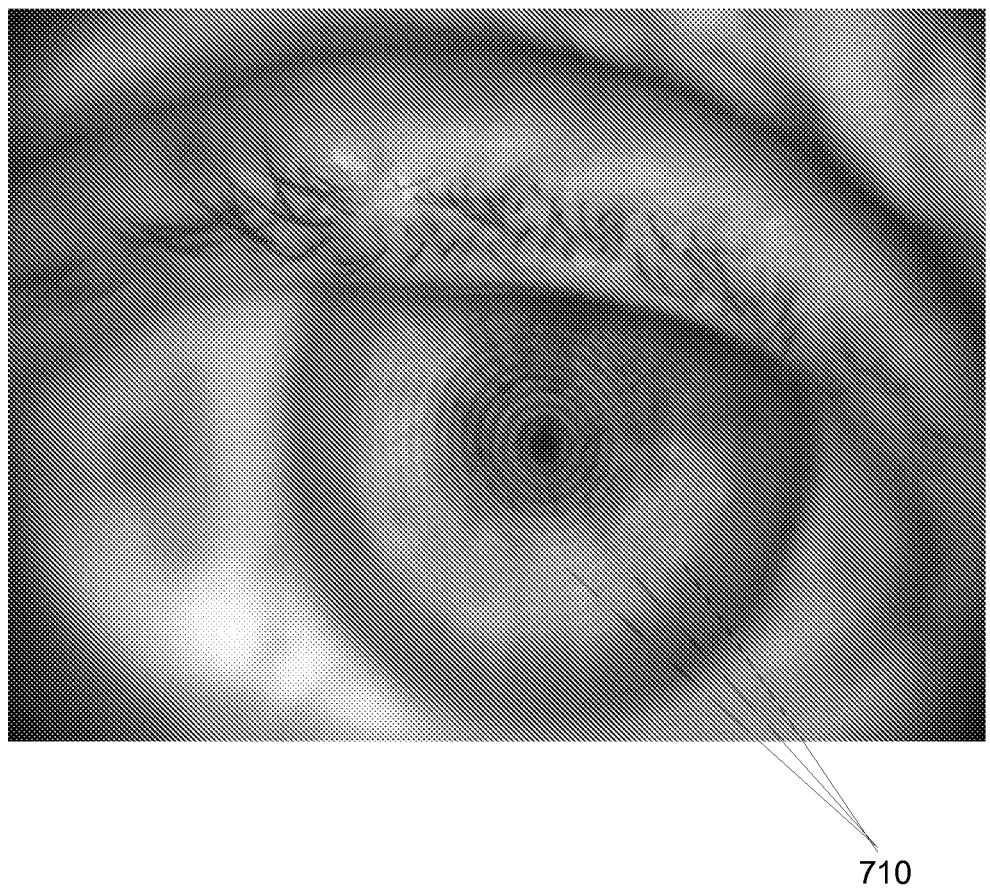
FIG. 7 is an example of a video image with corneal topography imaging according to some embodiments.

A3. Pachymetry Scan Pattern [2048, 4, (16+2), 1] with Corneal Topography Imaging Corneal topography instruments used in clinical practice are most often based on Placido-based reflective image analysis. As illustrated in FIG. 6b, optical imager 622 can be a corneal topography instrument. Corneal topography imaging uses the analysis of reflected images of multiple concentric rings 710 projected on the anterior surface of the cornea, as shown in FIG. 7. The reflected image is captured on a charge-coupled device (CCD) camera. Computer software in computer 608 then analyzes the data and displays the results, such as axial curvature map, tangential curvature map, elevation map, refractive power map, and high-order aberrations map.

One of the advantages using the corneal topography imaging is that the data is acquired almost simultaneously and therefore motion artifacts can be minimized. Another advantage is that the number (resolution) of data acquired in the 2D x-y plane is much greater (finer) than that from OCT imaging. However, the limitation that the posterior surface of the cornea cannot be imaged is a big drawback. All the maps and measurements related to posterior surface are estimated with some kind of mathematical models, leading to non-optimized results. Therefore, some embodiments of the present invention integrate the corneal topography imaging and OCT imaging as illustrated in FIG. 6b to produce more reliable measurements and results.

In some embodiments, a [2048, 4, (16+2), 1] scan configuration, with sixteen radial scans (n=16) plus two circular scans (c=2), repeated four times (r=4), in each scan set 100 with no repeat (m=1), can be used to create this scan pattern for pachymetry measurements.

The lengths of the radial and the circular segments can be determined based on the desired clinical applications. In some embodiments, the lengths of the radial segments can be about 11 mm and the diameters of the circular segment can be about 3 mm and 5 mm, respectively. The scan configuration is suitable for obtaining corneal pachymetry map along with corneal topography imaging to cover an area of interest of about 11 mm in diameter. The length of each radial scan, generally ranges from about 9 to about 11 mm, and the diameters of the circular scans can vary, depending on the area of interest. The approximate total scan time, with a=2048, for the resulting scan pattern 100 is $t=(2048 \times 4 \times (18) \times 1)/70,000 = 2.11$ sec, assuming a scan speed of 70,000 A-scans/second. The total scan time t will vary depending on the scan speed of the OCT scanner.

The details of scan order are similar to those described in Section A1 above. Different variations of scan parameters can be understood by one of ordinary skill in the art within the scope of the present invention. For example, a scan pattern can be designed as [2048, 1, (16+2), 4] where the radial scan has no repeat but each scan set is repeated four times (m=4).

One of the motivations to acquire more data is to better integrate OCT data with the results from the corneal topography imaging. Although the scan time is longer than the scan pattern without using corneal topography imaging (Section A1), the induced motion effect can be alleviated by replacing and post-processing the OCT anterior/posterior surface data with the corneal topography data. The post-processing methods such as motion correction and image registration can be used in the present invention.

A4. Angle-to-Angle (ATA) Scan Pattern [2048, 4, (16+2), 1]

Figure 14:
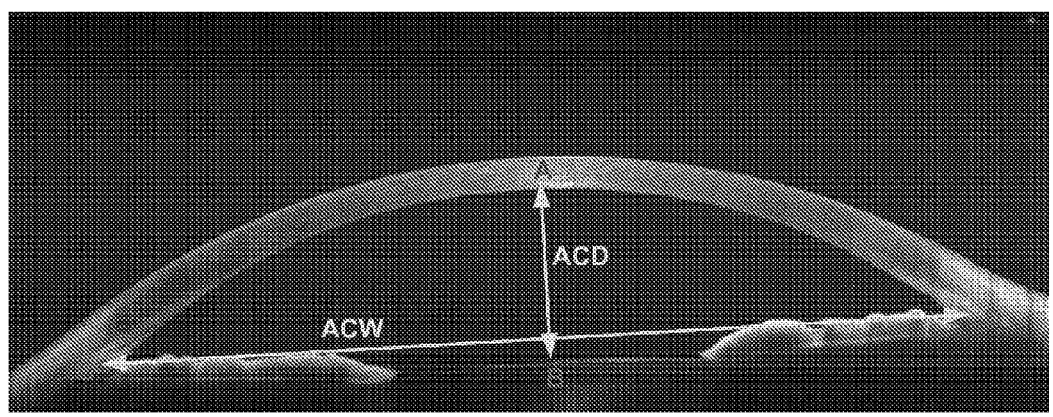
FIG. 14 shows an example of the measurements, ACD and ACW, computed from an Angle-to-Angle scan pattern.

In some embodiments, a scan configuration with sixteen radial scans plus two circular scans, repeated four times (r=4), in each scan set with no repeat (m=1) (scan pattern designation [2048, 4, (16+2), 1]) can be used to create a scan pattern for angle-to-angle measurement. The lengths of the radial and the circular segments can be determined based on the desired clinical applications. In some embodiments, the lengths of the radial segments are about 16 mm and the diameters of the circular segment are about 3 mm and about 5 mm. The scan configuration is suitable for obtaining Anterior Chamber Width (ACW), Anterior Chamber Depth (ACD), and various angle measurements such as Angle Opening Distance (AOD) and Trabecular Iris Space Area (TISA), as shown in FIG. 14. The length of each radial scan generally ranges from about 11 to about 16 mm, and the diameters of the circular scans can vary, depending on the area of interest. The approximate total scan time for scan pattern is $t=(2048 \times 4 \times (18) \times 1)/70,000 = 2.11$ sec, assuming a scan speed of 70,000 A-scans/second. The total scan time t will vary depending on the scan speed of the OCT scanner.

The details of scan order are similar to those described in Section A1. Different variations of scan parameters can be understood by one of ordinary skill in the art within the scope of the present invention. For example, a scan pattern can be designed as [2048, 1, (16+2), 4] where the radial scan has no repeat but each scan set is repeated four times (m=4). This scan pattern allows more data to be collected to better assess the various measurements in various radial directions and to better ensemble data for 3D presentation.

A5. Lens Scan Pattern [2048, 4, (0+4), 1]

In some embodiments, a configuration with four radial scans, repeated four times (r=4), in each scan set and such scan set has no repeat (m=1) is used to create this scan pattern for lens measurement. The lengths of the radial segments can be determined based on the desired clinical applications. In some embodiments, the lengths of the radial segments are 11 mm. The scan configuration is suitable for obtaining lens thickness at various radial directions. The length of each radial scan generally ranges from about 9 to about 11 mm and can vary depending on the area of interest. The approximate total scan time for scan pattern is $t=(2048 \times 4 \times 4 \times 1)/70,000 = 0.46$ sec, assuming a scan speed of 70,000 A-scans/second. The total scan time t will vary depending on the scan speed of the OCT scanner.

The details of scan order are similar to those described in Section A1. Different variations of scan parameters can be understood by one of ordinary skill in the art within the scope of the present invention. For example, a scan pattern can be designed as [2048, 1, (0+4), 4] where the radial scan has no repeat but each scan set is repeated four times (m=4). One motivation to acquire the data of multiple repeats is to perform scan average such that the top and bottom surfaces of the lens can be automatically and more reliably detected.

A6. Axial Length Scan Pattern [512, 1, 1*, 5]

Figure 8A:
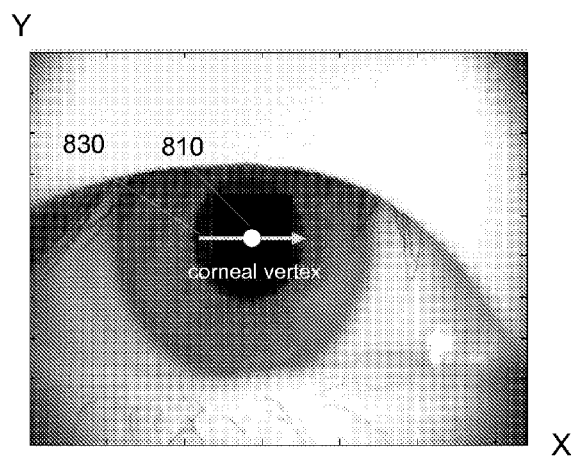
FIGS. 8a, 8b, and 8c show exemplary cornea and retina images simultaneously acquired for the axial length scan pattern.

The B-scan images of the cornea and retina can be simultaneously acquired by a [512, 1, 1*, 5] Axial Length scan pattern, where 1* indicates a single horizontal scan 120, in some embodiments of the present invention. This approach can be implemented by mounting a retina adaptor to a commonly-used anterior segment OCT scanner. As shown in FIG. 6b, optical imager 622 can be a retina adaptor. The user will then aim the center of the scan pattern at the corneal vertex 810, as shown in the video image FIG. 8a, and the brightest reflection spot confined in the pre-determined small box area 820 of the anterior corneal surface, as shown in the OCT B-scan image FIG. 8b. For the posterior segment (retina), an automated method can be invoked to perform the auto-Z (auto-alignment in Z direction) function to ensure that the retinal signal is present at the display window, as shown in FIG. 8c.

Figure 9:
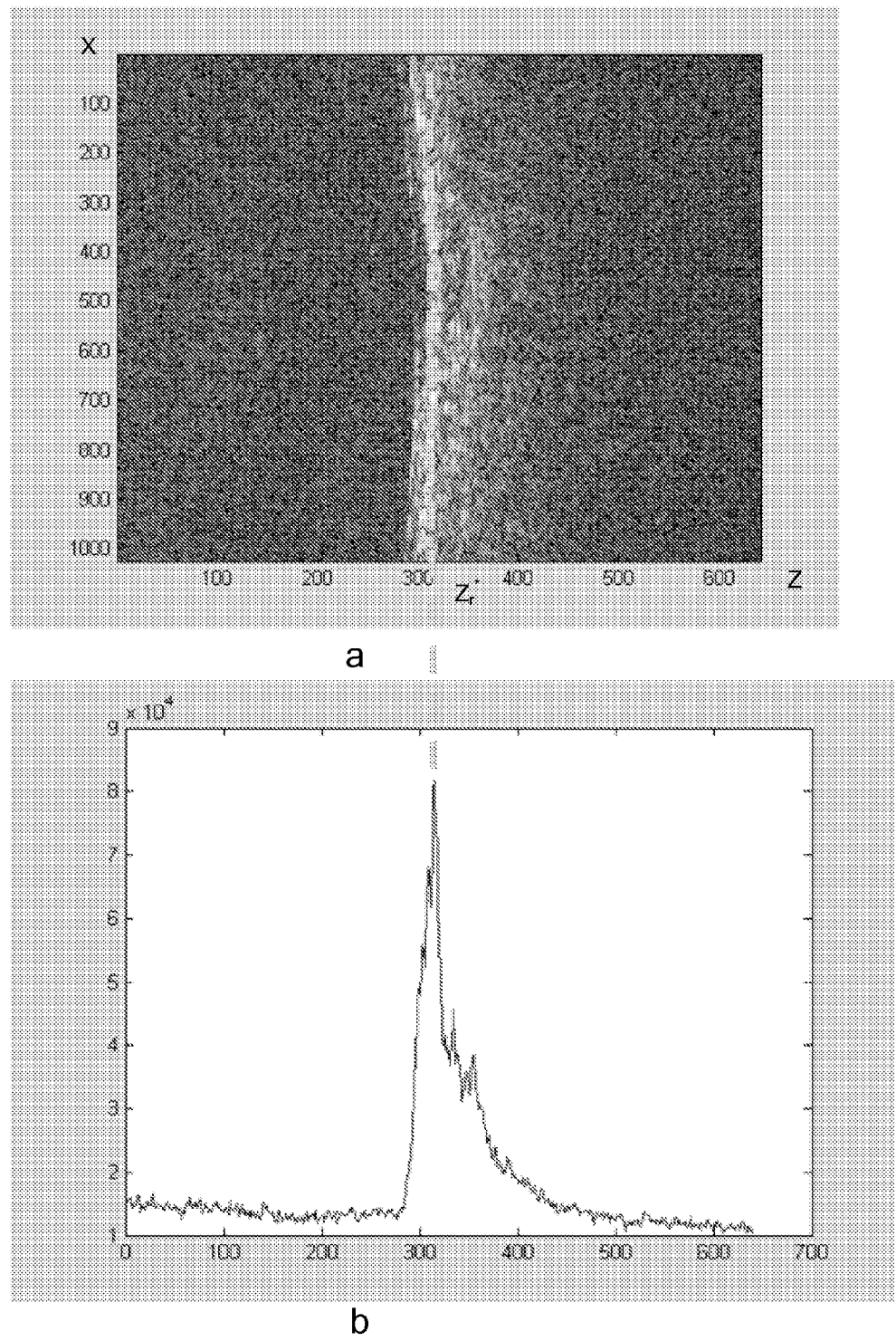
FIGS. 9a, and 9b show an example of locating the position of retinal RPE.

In some embodiments, a scan configuration with one horizontal raster scan, with no repeat (r=1), in each scan set and such scan set has five repeats (m=5) is used to create this scan pattern for axial length measurement. The lengths of the raster segments can be determined based on the desired clinical applications. In some embodiments, the lengths of the raster segments are about 1 mm in retina and about 2 mm in cornea. The scan configuration is suitable for obtaining the axial length measurement. As shown in FIG. 9a, the retinal RPE is relatively flat in the 1 mm range and therefore the peak of the intensity profile, by summing the intensity values in the x-(vertical) direction, would represent the retinal RPE position, $z_r^*$, in the z-(horizontal) direction, as shown in FIG. 9b. The length of the raster scan, generally ranges from about 0.5 mm to about 2.0 mm in the retina and from about 1.0 mm to about 4.0 mm in the cornea, can vary, depending on the area of interest. The approximate total scan time for scan pattern is t=(512×1×1×5)/70,000=0.04 sec, assuming a scan speed of 70,000 A-scans/second. The total scan time t will vary depending on the scan speed of the OCT scanner.

Figure 10:
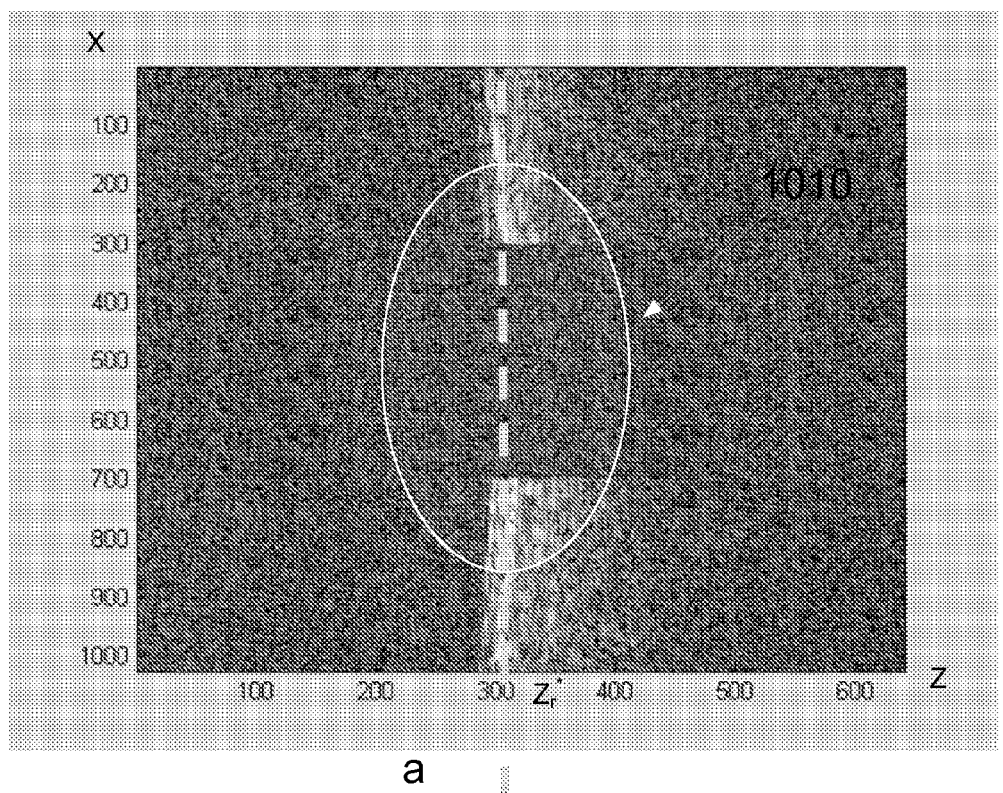
FIGS. 10a, and 10b show an example of locating the position of retinal RPE for a dense cataract patient.
Figure 10:
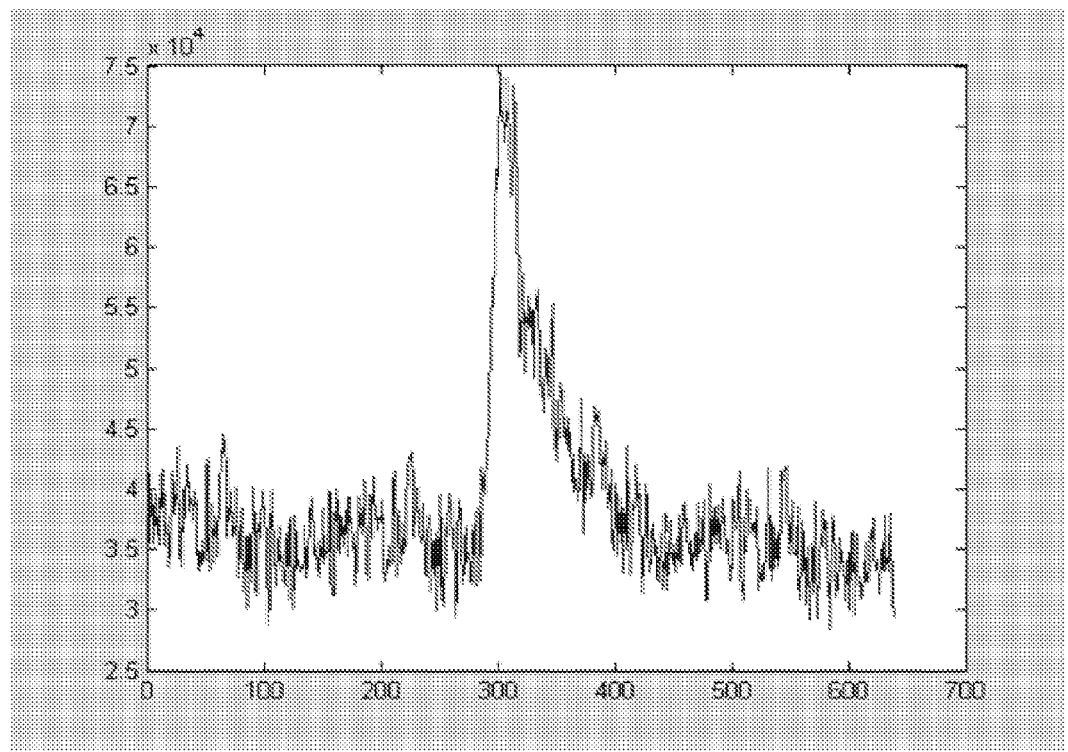

One advantage of using the scan pattern over some other current approach (e.g. IOL Master) is that it acquires data from multiple A-scans for more accurate measurement, rather than from simply one single A-scan. For dense cataract subjects, the embodiments of the scan pattern disclosed herein provide a better chance to locate the position of the retinal RPE, as shown in FIGS. 10a (retinal cross-sectional B-scan) and 10b (intensity profile of the cross-sectional area).

A7. Volumetric Axial Length Scan Pattern [512, 1, 9*, 5]

Extending the above one horizontal raster scan pattern (scanned at one y position) to the multiple horizontal raster scans (scanned at multiple y positions), a 512×9 grid of A-scans (total 4608 A-scans) can be taken to cover a 1×1 mm central retinal area (i.e. 9 B-scans, each of 512 pixel width) with a scan pattern designated as [512, 1, 9*, 5]. Such a pattern is illustrated in the video image of FIG. 11.

Figure 11:
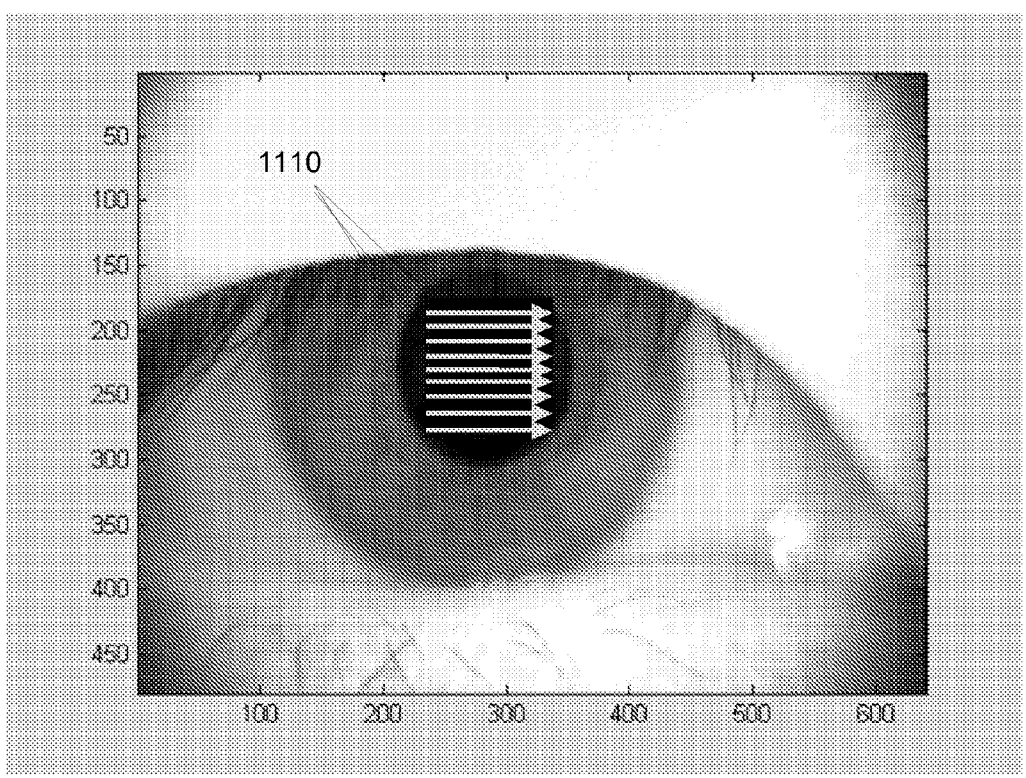
FIG. 11 shows an exemplary video image of a volumetric axial length scan pattern.

In the [512, 1, 9*, 5] scan configuration, there are nine horizontal raster scans 1110, with no repeat (r=1), in each scan set and such scan set has five repeats (m=5) to create this scan pattern. The lengths of the raster segments can be determined based on the desired clinical applications; preferably, the lengths of the raster segments are about 1 mm in retina and about 2 mm in cornea. The scan configuration is suitable for obtaining the axial length measurement, as illustrated in FIG. 11. The retinal RPE is relatively flat in the 1 mm range and therefore the peak of the intensity profile, by summing the intensity values in the x-(vertical) direction, represent the retinal RPE position in the z-(horizontal) direction similar to that shown in FIG. 9b. The length of the raster scan can range from about 0.5 mm to about 2.0 mm in the retina and from about 1.0 mm to about 4.0 mm in the cornea and can vary depending on the area of interest. The approximate total scan time for scan pattern is t=(512×1×9×5)/70,000=0.36 sec, assuming a scan speed of 70,000 A-scans/second. The total scan time t will vary depending on the scan speed of the OCT scanner.

One advantage of using the scan pattern over other current approach (e.g. IOL Master) and the scan pattern discussed in FIG. 8 is that it acquires A-scan data in a 2D (x-y) grid. For dense cataract patients, the volumetric scan pattern provides an even better chance to locate the position of the retinal RPE.

A8. Glaucoma and Retina Scan Pattern

Figure 19:
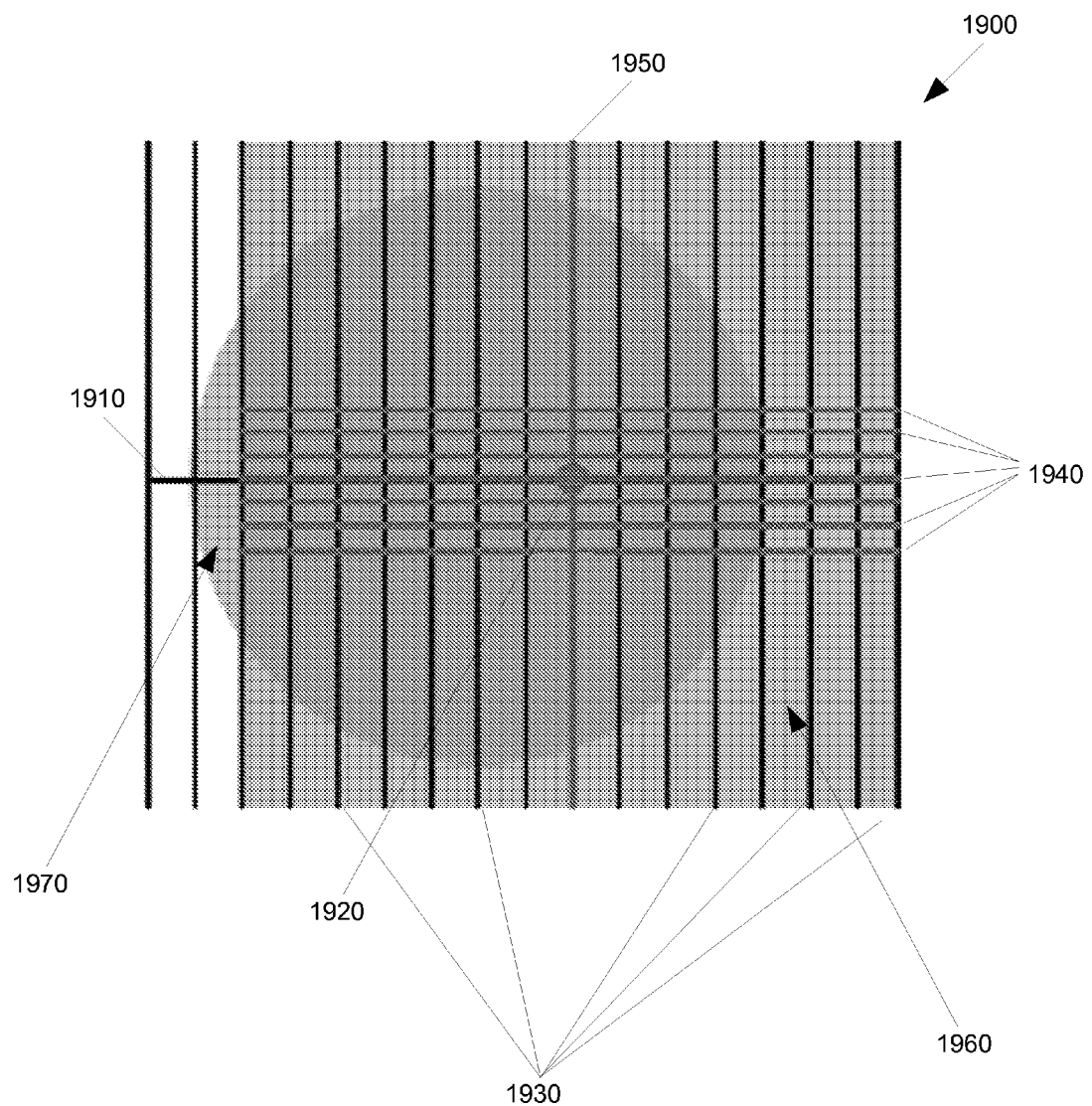
FIG. 19 shows an exemplary scan configuration suitable for glaucoma and retina.

FIG. 19 is an example of a comprehensive scan configuration that can be implemented in the OCT device discussed in FIG. 6a. This scan configuration uses a design approach to enhance utility and functionalities of a single scan configuration. In common practice, a single scan configuration is usually tailored to evaluate one single area of interest of particular pathology. In some embodiments of the present invention, scan configuration 1900 is designed to be capable of evaluating at least two pathologies with only one single scan, specifically retina and glaucoma. In the exemplary scan configuration in FIG. 19, it is comprised of one (1) horizontal scan line 1910 through the fovea 1920; 17 vertical scan lines 1930 spaced evenly apart; seven (7) horizontal scan lines 1940 average multiple times centering at or about the fovea 1920; and one (1) vertical scan line 1950 average multiple times centering on the fovea 1920. In some embodiments, the vertical scan lines 1930 are at 500 microns apart covering an area of 8×7 millimeter, the horizontal scan lines 1940 and the vertical scan line 1950 are averaged five times to enhance the image quality. This exemplary scan configuration consists of a total of 58 scan lines and takes approximately 2.3 seconds to complete using a similar device as discussed in FIG. 6 using a scan rate of approximately 26,000 A-scans/second; a higher scan speed can be achieved with a scan rate of 70,000 A-scans/second. A fixation pattern is generally required to guide the direction of the subject's eye in order to position the scan configuration at an area of interest. In the scan configuration 1900, a fixation pattern is preferably positioned slightly off center temporally for the particular area of interest.

This scan design allow user to obtain important data in at least two (2) areas of interest with one single scan. To evaluate the health of the retina using this scan configuration 1900, the scan lines overlapping with the retina area of interest 1960 can be used to generate data and image representation for analysis. To check for glaucomatous disease using scan configuration 700, the scan lines overlapping with the ganglion cell complex (GCC) area of interest 1970 can be used to generate data and image representation for analysis.

Scan configurations discussed in Section A1-A8 can provide useful high-resolution OCT data for further understanding of the object of interest. The following specifications describe various processing methods for these OCT data that can be used to generate useful image representation and quantitative evaluation of the object of interest.

Part B. OCT Data Processing

B1. Pachymetry Map

Figure 3A:
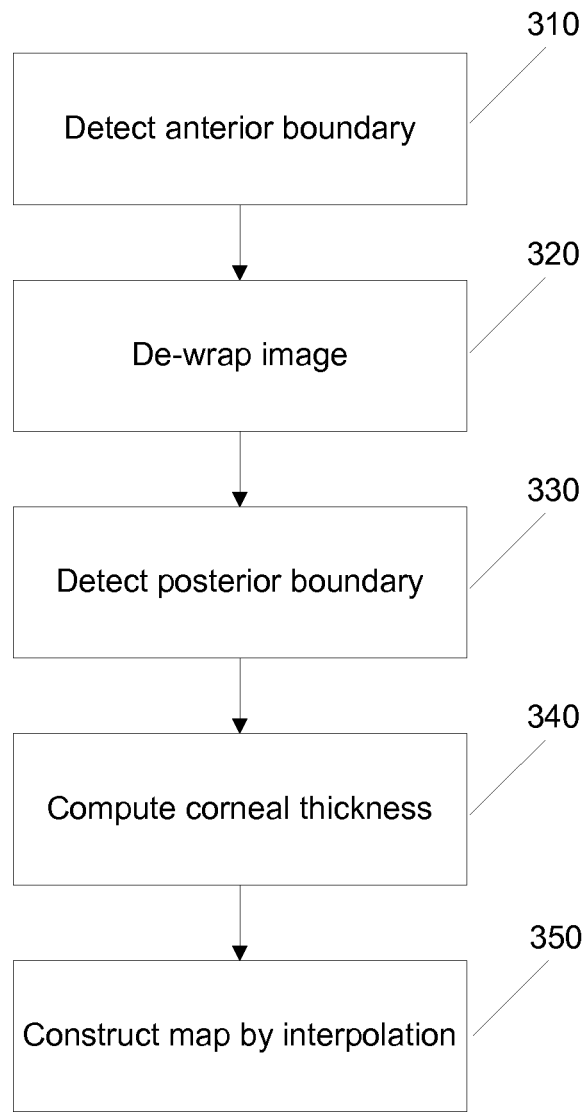
FIG. 3a is a flowchart illustrating acquisition of pachymetry images according to some embodiments of the present inventions.

FIG. 3a illustrates an exemplary flowchart that can be used to generate a 2D representation of the OCT data capable for pachymetry analysis. The flowchart in FIG. 3a can be implemented on computer 608. This 2D representation for pachymetry application is commonly called a pachymetry map in the field of ophthalmology. OCT system 600, as disclosed in FIG. 6 using the scan configuration as described in FIG. 1, is a noncontact method and can be used to generate pachymetry information for the cornea. The pachymetry map using scan pattern 100 as described in FIG. 1 can provide important characteristics of the cornea, such as thickness and surface curvature and continuity. Such information can be used to evaluate the corneal health of a subject eye and other ocular diseases, such as glaucoma. Corneal pachymetry is also particularly essential prior to a LASIK procedure to ensure sufficient corneal thickness to prevent abnormal bulging out of the cornea.

As illustrated in FIG. 3a, the first step to generate the pachymetry map is to detect the anterior boundary of the cornea surface using OCT data from a scan configuration in step 310. The scan pattern 100 utilized in step 310 can, for example, be the [1024, 2, (12+1), 3] scan pattern described above in section A1. Surface and layer segmentation are commonly performed in OCT data to evaluate different layers and regions of interest. Different algorithms are available for layer segmentations, such as, edge detection by Sobel or Canny operator. After the anterior boundary has been detected in step 310, the next step, step 320 is to de-warp the image. An unprocessed OCT image is distorted by refraction at the air-cornea and cornea-aqueous interfaces due to the difference in the speed of light in air, cornea, and aqueous medium. Differences in the index of refraction of different media impact the speed of light traveling through the medium. Since the index of refraction of these media are known to a high precision, image processing can be performed with high accuracy to remove the distortion caused by the difference in the index of refraction of the different medium. After the distortion is removed in step 320, the posterior surface boundary can then be detected in step 330. A similar algorithm used to perform the layer segmentation in step 310 can be used for detecting the posterior boundary in step 330. Once these two important layers of interest of the cornea are detected, different characteristics of the cornea can be obtained.

Figure 3B:
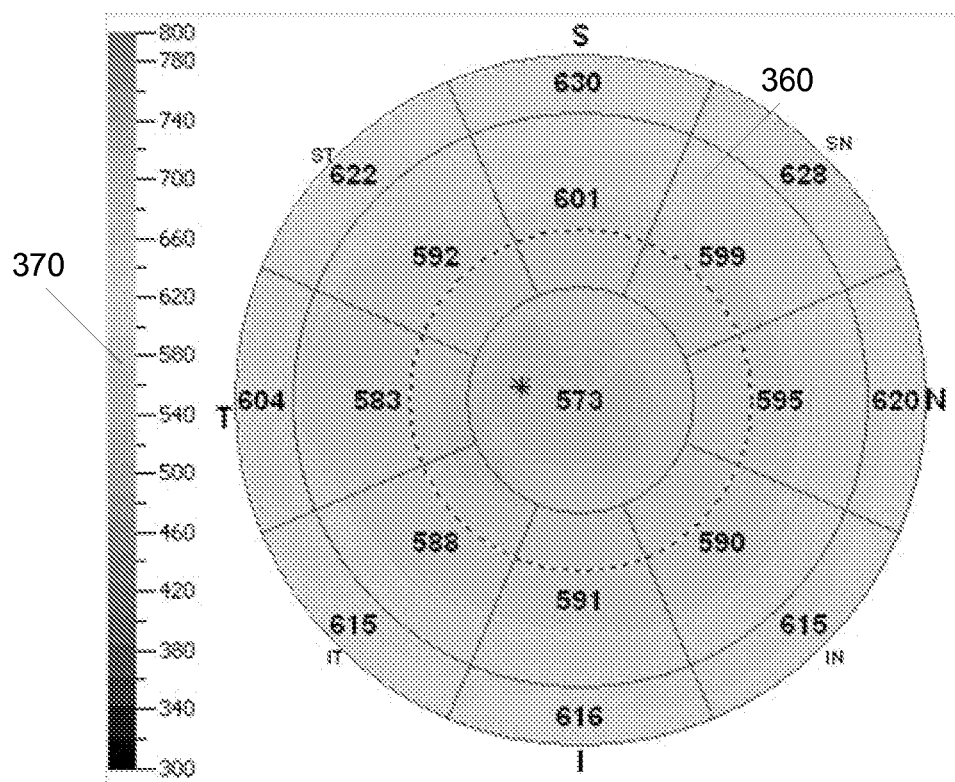

A common measurement of interest is the thickness of the cornea. The thickness of the cornea can be calculated in step 340. The corneal thickness can be defined as the distance between the anterior boundary and the poster boundary. The last step to generate a pachymetry map is to perform interpolation in step 350. The distance between the two boundaries are calculated for each of the radial scans 101-112. Interpolation can then be performed to estimate the thickness values not captured by the radial scans. Such interpolation can be performed using one or multi-dimensional interpolation, with interpolation method, such as bi-linear interpolation, bi-cubic interpolation or spline interpolation, as are commonly used in the field. A gray scale or color map can be applied to the interpolated data to create the pachymetry map. FIG. 3*b* is an example of a pachymetry map with the thickness value 360 corresponding to the values indicated in the adjacent color bar 370. Pixels with brighter color represent location with higher thickness values and the darker pixels represent lower thickness values.

B2. Computation of Corneal Power

Figure 4:
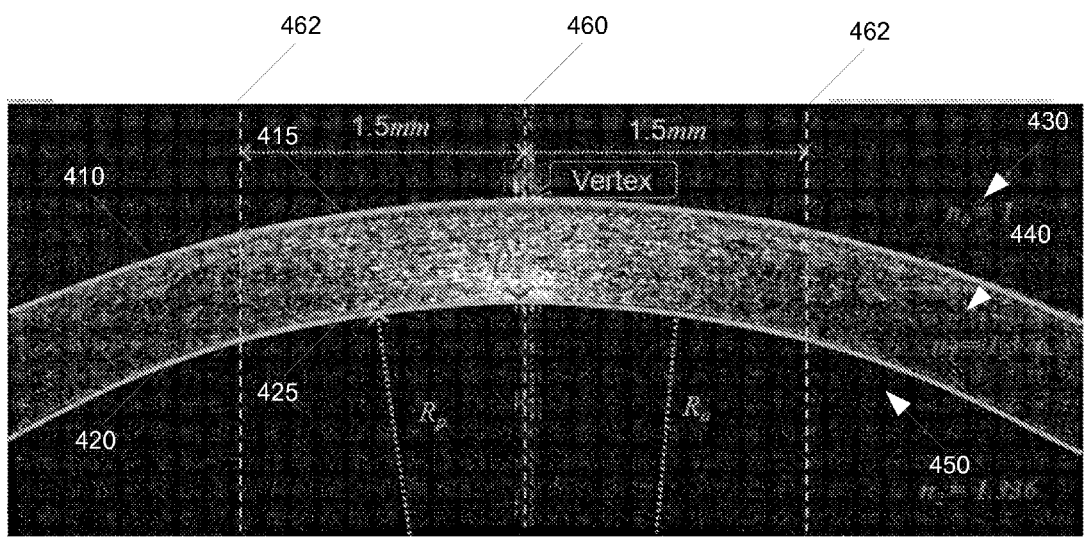
FIG. 4 shows an example of a cross sectional cornea image.

FIG. 4 shows an example of a cross sectional cornea image. Corneal power is the ability of the cornea to refract light and focus objects onto the retina. Corneal power is different in the anterior surface 410 and the posterior surface 420 due to the difference in refractive index of different medium. As illustrated in the example of FIG. 4, when light rays of an object enters the eye, the light passes through the air medium 430, with index of refraction $n_0=1$, then to the cornea medium 440, with index of refraction $n_1=1.376$, and then to the aqueous medium 450, with index of refraction $n_2=1.336$, before it reaches the retina. Other parameters may be utilized (e.g., the aqueous medium 450 may have a different index of refraction).

Figure 5:
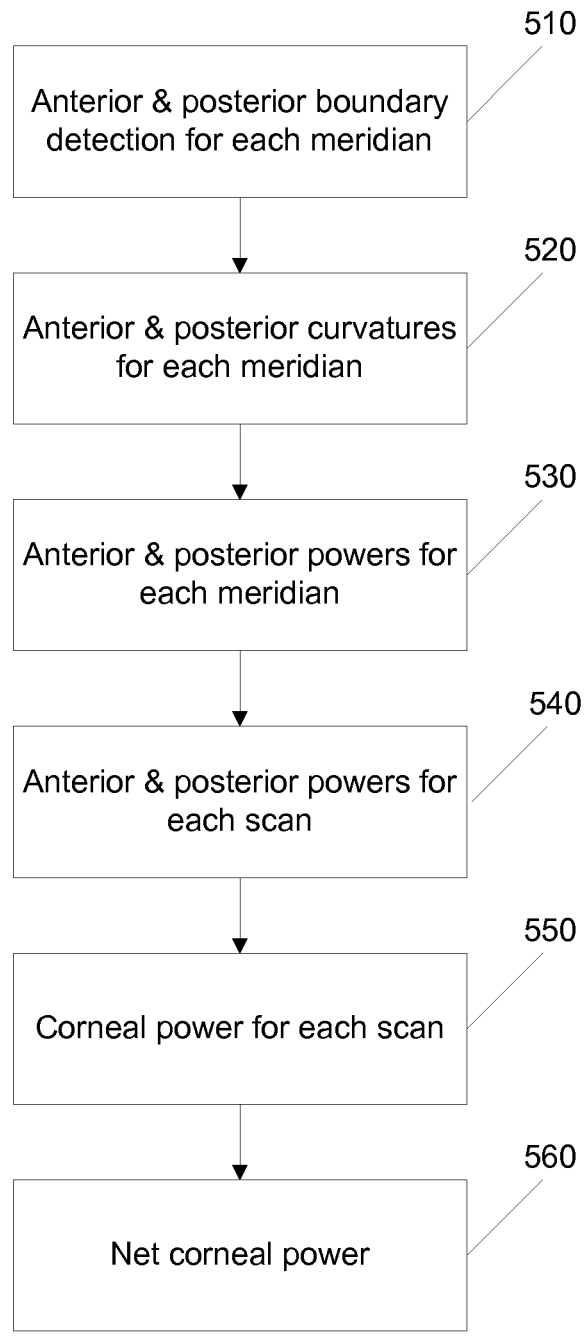
FIG. 5 is a flowchart illustrating acquisition of net corneal power according to some embodiments of the present inventions.

An exemplary flowchart that can be implemented on computer 608 to calculate the net corneal power is shown in FIG. 5. OCT data may, for example, be obtained utilizing the scan pattern [1024, 2, (8+1), 3] as discussed above in Section A2. The first step 510 is to perform anterior and posterior boundary detection for each meridian. A meridian is the OCT data obtained from each of the scan lines 201-208 in FIG. 2. A similar boundary detection method as discussed in the generation of pachymetry map in FIG. 3 can be used in this step. A 3 mm region centered on the corneal vertex 460 of the cornea as described above can be selected to determine the cornea power for the central region. The central 3 mm region is demarked by the vertical dashed lines 462 in FIG. 4, with 1.5 mm equidistant from the corneal vertex 460. The next step 520 is to determine the anterior and posterior curvatures for each meridian using best fit within the 3 mm region. An example of the anterior and posterior curvature is shown as the highlighted curves 415 and 425, respectively. The next step is to determine the anterior and posterior refractive powers for each meridian in step 530. The anterior refractive power can be calculated using the following equation:

$$K = (n_{after} - n_{before})/R,$$

where K is the refractive power of the surface, $n_{after}$ is the index of refraction of the medium after the surface, $n_{before}$ is the index of refraction of the medium before the surface, and R is the radius of curvature of the surface. For anterior refractive power, the power is designated as $K_a$, $n_{after}=n_1$, $n_{before}=n_0$, and $R=R_a$, the radius of curvature of the anterior surface, as shown in FIG. 4. Similarly, for posterior refractive power, the power is $K_p$, $n_{after}=n_2$, $n_{before}=n_1$, and $R=R_p$, the radius of curvature of the posterior surface.

$K_a$ and $K_p$ for each meridian from scans 201-208 in FIG. 2 are then calculated and averaged to obtain the anterior and posterior powers for each scan 540. After the anterior and posterior power of each scan is determined, the corneal power for each scan 550 can be calculated using a thick lens formula:

$$K = \overline{K}_a + \overline{K}_p - \frac{\overline{D}}{n_1} \times \overline{K}_a \times \overline{K}_p,$$

where K is the corneal power for each scan, $\overline{K}_a$ is the averaged anterior power of each meridian, $\overline{K}_p$ is the averaged posterior power of each meridian, $n_1$ is the index of refraction of the cornea, and $\overline{D}$ is the average thickness between the anterior fitted boundary 415 and the posterior fitted boundary 425.

Step 510 to step 550 can then be repeated for each of the desired repeated scan to improve the reliability and accuracy of the power calculation. The last step to estimate the net corneal power 560 is to obtain the median of the corneal powers from 3 repeated scan having the smallest differences from each other.

B3. Processed Data Alignment with Other Imaging Modalities

Processed OCT data, such as the pachymetry map discussed above, is capable of providing useful information for clinical use. The utility of the OCT data acquired can be further enhanced when combined with other imaging modality. According to some embodiments of the present invention, the OCT data can be aligned to images acquired by corneal topography system to provide side-by-side topographic and tomographic information simultaneously for better clinical functionalities.

OCT data can be aligned to images by other imaging modality through identification of landmarks. Cornea is a convex surface with an apex generally at or close to the center of the cornea in the x-y plane. The corneal vertex from the OCT data obtained using the scan configurations in FIG. 1 can be detected by finding the coordinates of the pixel with the strongest reflection intensity in each of the OCT radial scans and can be used as a useful landmark for alignment. Intensity profiling histogram can be used to reliably detect the corneal vertex in OCT data. For example, the x and y locations of the corneal vertex can be determined by the x-location of the horizontal OCT (x-z) scan and the y-location of the vertical OCT (y-z) scan, respectively. Corneal vertex provides an accurate estimate of the center of the cornea that can help align OCT data to corneal topography maps generated by other imaging modalities, such as Placido-based topography systems.

In some situations, due to different corneal anatomy, an iris center or pupil center can be used as a landmark to locate the center of the cornea in order to combine the OCT data with other modalities instead of using the corneal vortex. According to some embodiments, a sequence of iris video images can be captured in sync with the OCT radial and circular scans as described in FIG. 1. Image processing techniques based on dynamic thresholding and boundary detection as described above can be used to locate the pupil center in the iris video images. Image registration can then be used to find the x and y locations of the OCT data relative to the pupil center.

Figure 12:
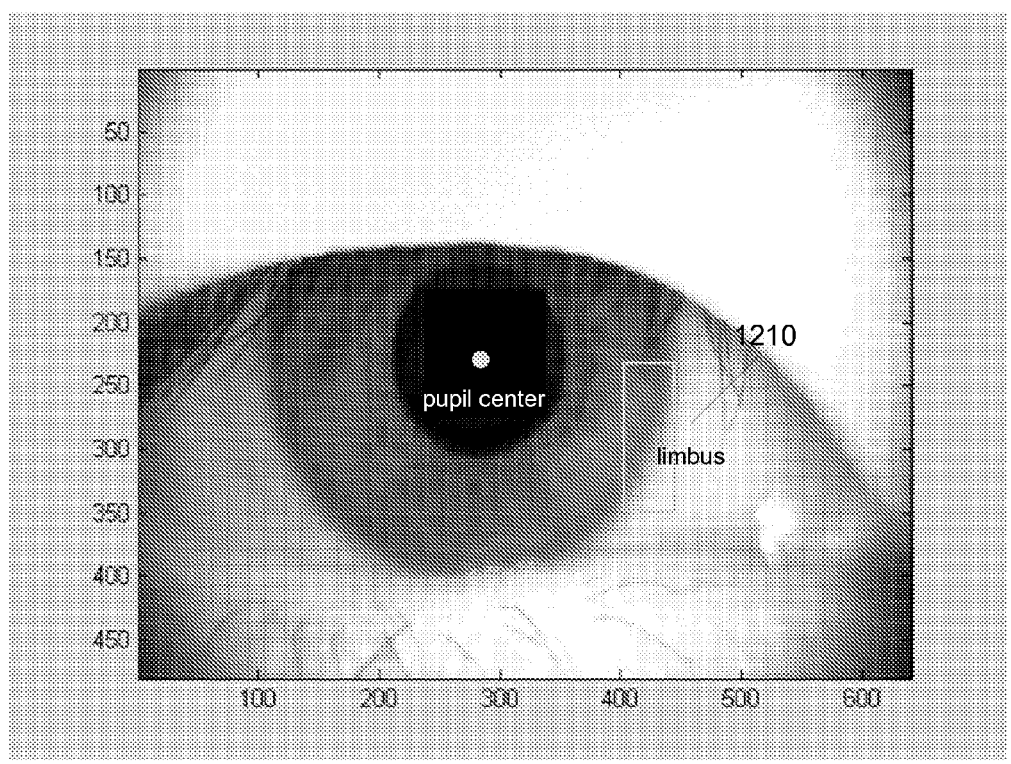
FIG. 12 shows a video image of the pupil center and the limbus as the anatomical landmarks for the data registration and motion correction in some embodiments of the present inventions.

According to some embodiments, the corneal limbus 1210 at the border of the cornea and the sclera (the white of the eye), as shown in FIG. 12, can be used as the anatomical landmark for data alignment and registration. In some embodiments of the present invention, the elevation map of the anterior corneal surface derived from the OCT pachymetry map is registered against the elevation map generated from the corneal topography imaging.

B4. Corneal Power Maps

Figure 13:
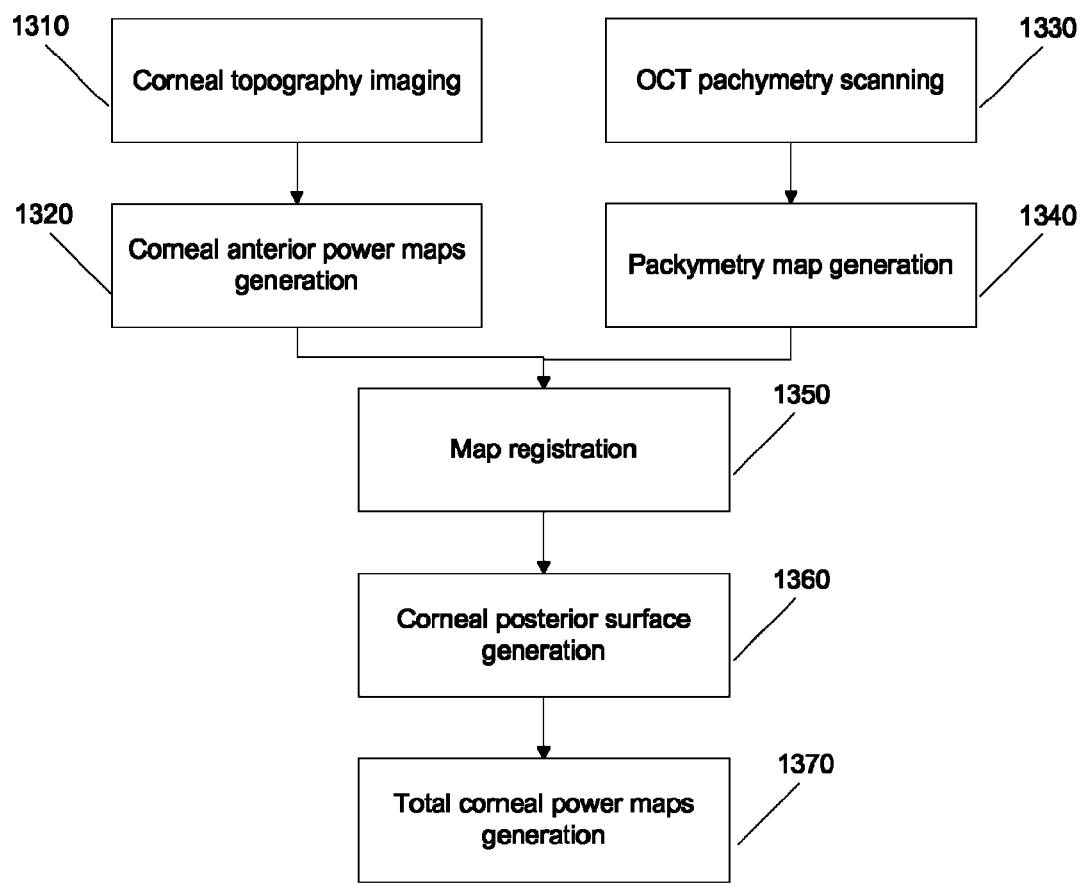
FIG. 13 is a flowchart illustrating acquisition of the posterior and total corneal power maps according to some embodiments of the present inventions.

FIG. 13 is an exemplary flowchart that illustrates the generation of the total corneal power maps by integrating the corneal topography imaging 1310 and OCT pachymetry scanning 1330. There are at least five corneal anterior power maps 1320 that can be generated from the topography imaging as discussed above; namely, axial curvature map, tangential curvature map, elevation map, refractive power map, and high-order aberrations map. With respect to the OCT pachymetry scanning, at least one pachymetry map 1340 can be generated from the OCT pachymetry scanning. The computational method for the OCT pachymetry map generation was described in Section B1 above. In the map registration step 1350, pachymetry map is registered against the sequence of video images acquired during the OCT scanning step 1330, or, the elevation map generated from the data acquired in the corneal topography imaging step 1310. After the map registration, the corneal posterior surface, $S_p$ (x,y), can be readily obtained by $$S_p(x,y)=S_a(x,y)+T(x,y),$$

where $S_a$ (x,y) and T (x,y) represent the anterior surface (z value) and the corneal thickness value at the spatial position (x,y), respectively. Once the posterior surface $S_p$ (x,y) is determined and its associated power map, $K_p$ (x,y) is computed, the total corneal power map, K (x,y), can be readily obtained by $$K(x,y)=K_a(x,y)+K_p(x,y)$$

where the anterior power map $K_a$ (x,y) was computed by the image analysis of corneal topography data.

B5. Angle-to-Angle (ATA) Measurements

As shown in FIG. 14, the Anterior Chamber Depth (ACD) is interpreted as the distance between the posterior vertex of the cornea (point A) and the anterior vertex of the eye lens (point B). The Anterior Chamber Width (ACW) is the horizontal diameter between two angle points C and D. The angle points are determined by the intersections of the extrapolated curves of the posterior corneal curve and the anterior iris curve. The ACW has also been defined by the horizontal diameter of the iris roots in some literature.

Figure 15:
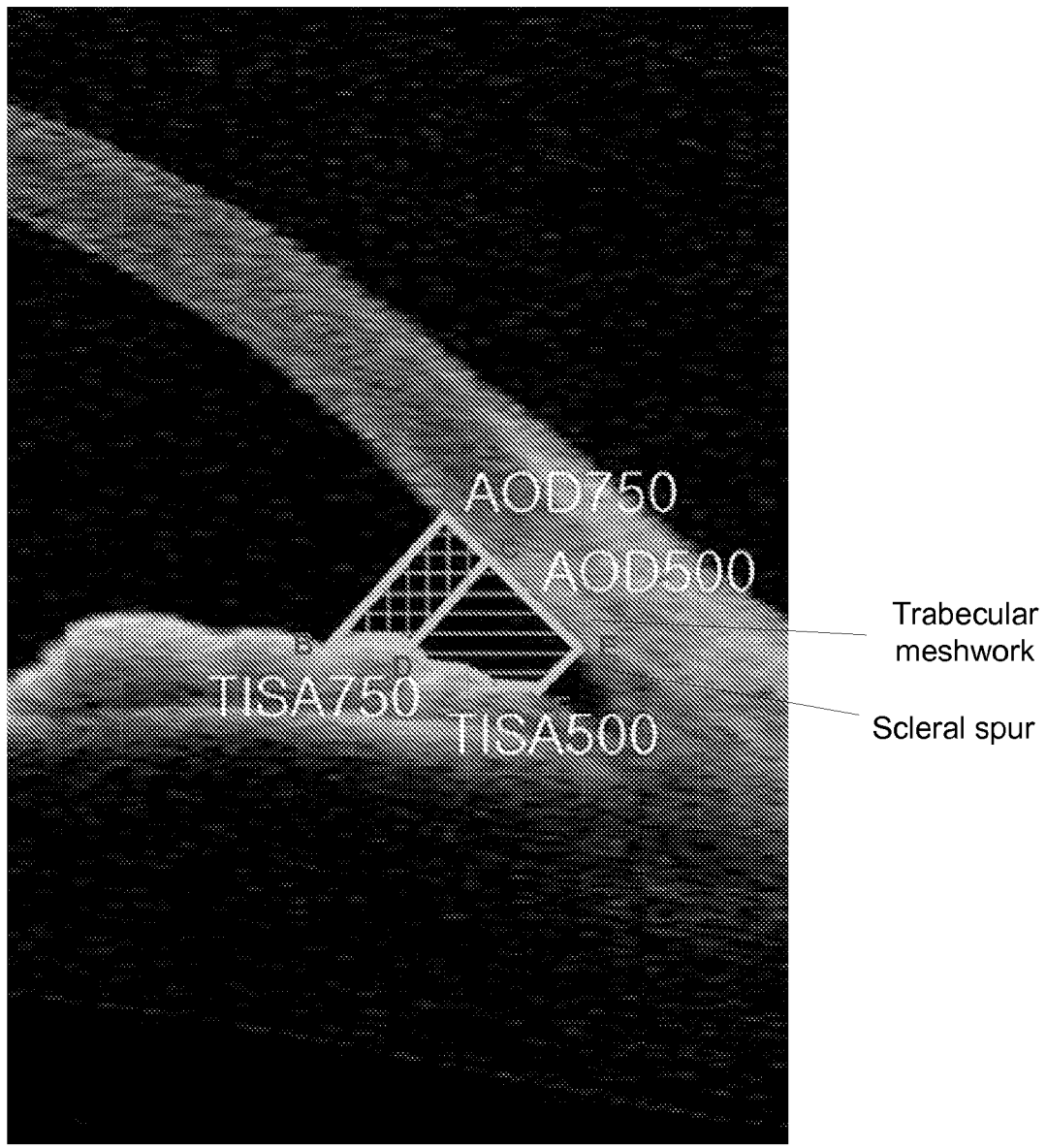
FIG. 15 shows another example of the measurements, AOD500, AOD750, TISA500, and TISA750, computed from the Angle-to-Angle scan pattern.

As shown in FIG. 15, the Angle Opening Distance (AOD) at about 500 μm (segment CD) anterior to the scleral spur (point E) (AOD500) and the AOD at about 750 μm (segment AB) anterior to the scleral spur (point E) (AOD750) are defined as the distance from the corneal endothelium to the anterior iris perpendicular to a line drawn along the trabecular meshwork at about 500 μm or 750 μm from the scleral spur (point E). The Trabecular-Iris Space Areas (TISA) at about 500 μm or 750 μm from the scleral spur, TISA500 (region CDFE) or TISA750 (region ABFE), are defined as the areas bounded by the corneal endothelium, trabecular meshwork, and anterior iris surface out to a distance of about 500 μm or 750 μm from the scleral spur (point E).

These measurements may be clinically useful for the diagnosis of various ocular pathologies such as open angle glaucoma and closed angle glaucoma. In the preferred embodiments of the present invention, these parameters are computed automatically. In addition, a number of computer-assisted user-interface tools can be supplemented for manual calipers, including the corneal flap thickness tool, angle AOD tool, angle TISA tool, ACW/ACD tool, and Phakic IOL tool.

B6. Lens Measurements

Figure 16:
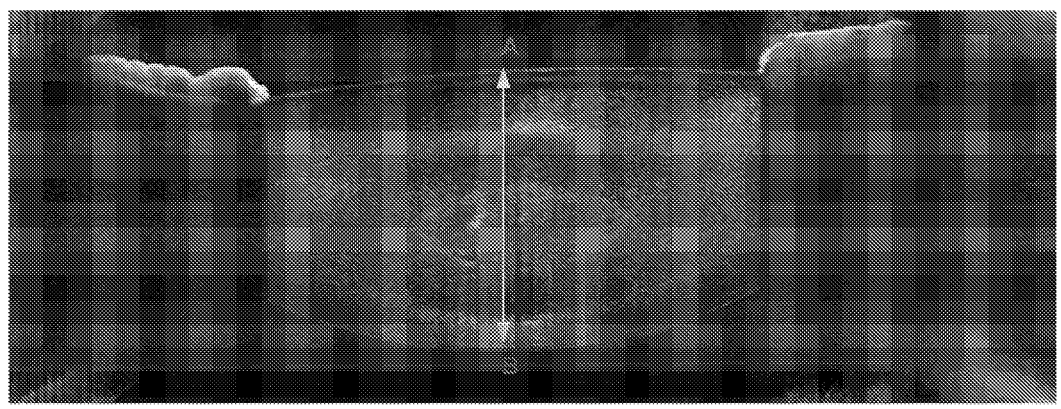
FIG. 16 shows an example of the lens thickness measurement computed from a lens scan pattern.

Lens thickness is important in IOL power calculation formulas. This measurement precludes the need for a separate immersion ultrasound procedure and saves valuable time by streamlining the examination process. As shown in FIG. 16, the lens thickness is measured from the top (point A) to the bottom (point B) of the lens. In addition, the opacity of the lens can be assessed. In the preferred embodiments of the present invention, these parameters are computed automatically. A number of computer-assisted user-interface tools can be supplemented for manual calipers, including lens thickness tool and lens opacity tool.

B7. Axial Length (AL) Measurements

Figure 17:
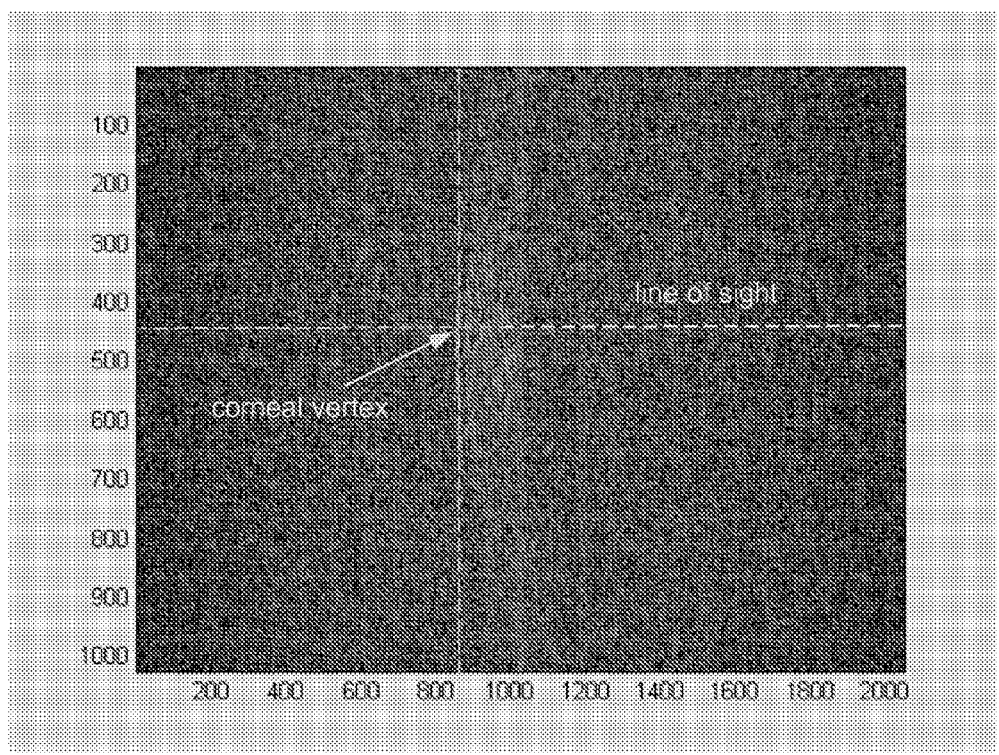
FIG. 17 shows an example of detecting the corneal vertex.

The axial length is the distance from the corneal vertex to the retinal RPE along line of sight. As shown in FIG. 8a, multiple A-scans (or a B-scan) 830 have been applied to acquire the corneal image and retina image simultaneously. The corneal vertex position is detected by locating the brightest spot ($z_c^*$, x*), where the $z_c^*$ is the corneal vertex z position in A-scan (in-tissue) direction, and x* is the position along line of sight, as shown in FIG. 17. The retinal RPE $z_r^*$ position can be detected by locating the peak of the intensity profile which sums or averages all the intensity values in the x-(vertical) direction, as shown in FIG. 9b. For dense cataract patients, portion of the retinal signal may be blocked 1010. Nevertheless, The retinal RPE $z_r^*$ position can still be detected by locating the peak of the intensity profile, as shown in FIG. 10b.

Figure 8B:
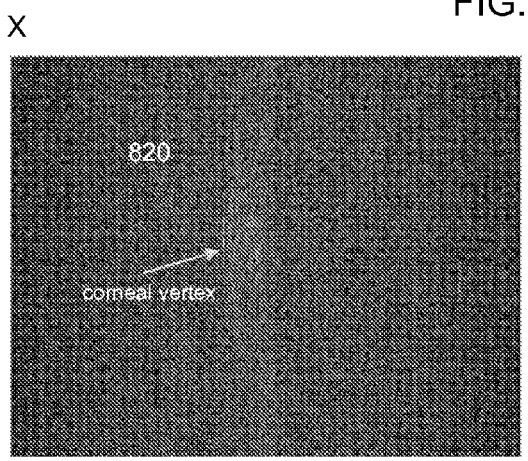
Figure 8C:
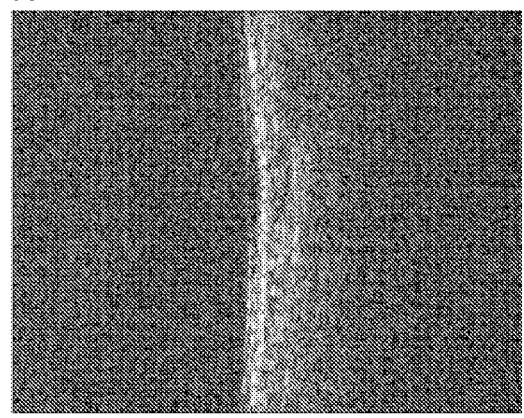

For the measurement based on the volumetric axial length scan pattern, the corneal vertex detection and retinal position determination can be performed similarly except for the multiple B-scans in the y-direction (i.e. into/out page in FIGS. 8b and 8c.) The corneal vertex position is detected by locating the brightest spot ($z_c^*$, x*, y*), where the $z_c^*$ is the corneal vertex z position in A-scan (in-tissue) direction, (x*, y*) is the position along line of sight. The retinal RPE $z_r^*$ position can be detected by locating the peak of the intensity profile which sums or averages all the intensity values in the x-(vertical) and y-(into/out page in FIG. 9 or 10) directions.

An adjustment factor can be added to match the AL measurement with ultrasound measurement or to the position of retinal ILM. Another adjustment factor can be added to match the AL measurement to the position of retinal IS/OS layer.

Figure 18:
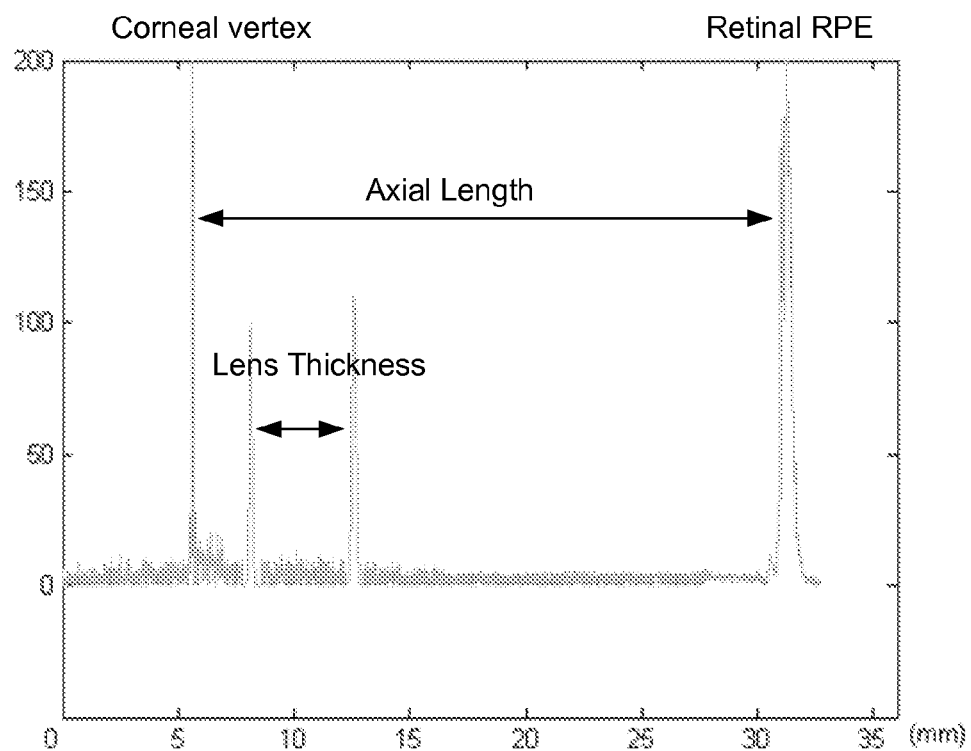
FIG. 18 shows an example of representing the axial length measurement in an intensity profile with the addition of the lens thickness intensity profile from FIG. 16.

In some embodiments of the present invention, the axial length measurement is represented by the intensity profile with the addition of the lens thickness, as shown in FIG. 18.

It should be appreciated that alternative and modifications apparent to one of ordinary skills in the art can be applied within the scope of the present inventions. For example, the OCT scan speed, scan length, different value for scan configuration design parameters, orientation and number of repeated meridian and scan can be varied from the specific embodiments disclosed herein.

We claim:

1. A method of eye examination, comprising:
   acquiring OCT data with a scan pattern centered on an eye cornea that includes n radial scans repeated r times, c circular scans repeated r times, and n* raster scans where the scan pattern is repeated m times, where each scan includes a A-scans, and where n is an integer that is 0 or greater, r is an integer that is 1 or greater, c is an integer that is 0 or greater, n* is an integer that is 0 or greater, m is an integer that is 1 or greater, and a is an integer greater than 1, the values of n, r, c, n*, and m being chosen to provide OCT data;

obtaining a corneal topography image; and
processing the OCT data by
    obtaining a pachymetry map from the OCT data,
    obtaining a corneal anterior power map from the corneal topography image,
    registering the pacymetry map with the corneal anterior power map,
    generating a corneal posterior surface, and
    generating a total corneal power map.

2. The method of claim 1, wherein the pachymetry map scan pattern is defined by a=1024, r=2, n=12, c=1, n*=0, and m=1.

3. The method of claim 1, wherein the Pachymetry scan is defined by a=2048, r=4, n=16, c=2, n*=0, and m=1.

4. The method of claim 1, wherein processing the OCT data further includes
    detecting an anterior boundary;
    de-wrapping OCT images from the OCT data;
    detecting a posterior boundary;
    computing corneal thickness; and
    constructing a corneal thickness map.

5. The method of claim 1, wherein processing the OCT data further includes
    determining anterior and posterior boundary for each radial scan;
    determining anterior and posterior curvatures for each radial scan;
    determining anterior and posterior powers for each radial scan;
    determining anterior and posterior powers for each scan;
    determining the corneal power for each scan; and
    determining the net corneal power.

6. An OCT imaging system, comprising:
an OCT imager that acquires OCT data with a scan pattern centered on an eye cornea that includes n radial scans repeated r times, c circular scans repeated r times, and n* raster scans where the scan pattern is repeated m times, where each scan includes a A-scans, and where n is an integer that is 0 or greater, r is an integer that is 1 or greater, c is an integer that is 0 or greater, n* is an integer that is one or greater, m is an integer that is 1 or greater, and a is an integer greater than 1, the values of n, r, c, n*, and m being chosen to provide OCT data;
a corneal topography imager that acquires a corneal topography image; and
a computer that processes the OCT data and the corneal topography image, the processing including
    obtaining a pachymetry map from the OCT data,
    obtaining a corneal anterior power map from corneal anterior image,
    registering the pacymetry map with the corneal topography power map,
    generating a corneal posterior surface, and
    generating a total corneal power map.

7. The system of claim 6, wherein the pachymetry map scan pattern is defined by a=1024, r=2, n=12, c=1, n*=0, and m=1.

8. The system of claim 6, wherein the pachymetry scan is defined by a=2048, r=4, n=16, c=2, n*=0, and m=1.

9. The system of claim 6, wherein the processing further includes
    detecting an anterior boundary;
    de-wrapping OCT images from the OCT data;
    detecting a posterior boundary;
    computing corneal thickness; and
    constructing a corneal thickness map.

10. The system of claim 6, wherein the processing further includes
    determining anterior and posterior boundary for each radial scan;
    determining anterior and posterior curvatures for each radial scan;
    determining anterior and posterior powers for each radial scan;
    determining anterior and posterior powers for each scan;
    determining the corneal power for each scan; and
    determining the net corneal power.

* * * * *